United States Patent [19]

Lyons

[11] 4,123,445
[45] Oct. 31, 1978

[54] NOVEL HOMOGENEOUS TRANSITION-METAL CATALYZED GEOMETRIC ISOMERIZATION OF CYCLIC EPOXY ALCOHOLS

[75] Inventor: James E. Lyons, Wallingford, Pa.

[73] Assignee: Sun Ventures, Inc., St. Davids, Pa.

[21] Appl. No.: 523,310

[22] Filed: Nov. 13, 1974

[51] Int. Cl.$^2$ ............................................. C07D 301/00
[52] U.S. Cl. ........................... 260/348.12; 260/348.55
[58] Field of Search ........................ 260/348 C, 348.12

[56] References Cited

U.S. PATENT DOCUMENTS 3,644,430   2/1972   Schulte-Elte .................. 260/348.57

Primary Examiner—Norma S. Milestone
Attorney, Agent, or Firm—J. Edward Hess; Donald R. Johnson; Stanford M. Back

[57] ABSTRACT

Geometrical isomerization of cyclic epoxy alcohols such as cis- or trans-1,2-epoxy-3-hydroxycyclohexane may be equlibrated by the use of soluble transition metal complexes having the formula $$L_x M^n X_y$$

wherein L is a neutral ligand such as a phosphine, arsine, stibine, amine, olefin, diene, CO or the like, $x$ is an integer of from 0–6 but when $x$ is 2 or more L may be the same or different; M is a Group VIII metal; $n$ is an integer of from 0–3 and denotes the valence state of the metal; X is an anionic ligand such as hydrogen, chloride, bromide, iodide, lower alkyl, trichlorostanato, cyano or the like; $y$ is an integer of from 0–3 which is equal to $n$ but when $y$ is 2 or 3, X may be the same or different. When $n$ is 0, then $x$ equals at least 1, but when either $x$ or $y$ is 0, then the other integer must be at least 1.

6 Claims, No Drawings

NOVEL HOMOGENEOUS TRANSITION-METAL CATALYZED GEOMETRIC ISOMERIZATION OF CYCLIC EPOXY ALCOHOLS

CROSS-REFERENCE TO RELATED CASES

This case relates to the following earlier filed cases:

| Serial No. | Title | Inventor | Filing Date |
|---|---|---|---|
| 393,514 | Preparation of Epoxyols Using a Vanadium Catalyst | Lyons | 8/31/73 |
| 375,229 | Resorcinol From 1,2-Epoxy-3-Hydroxycyclohexane | Lyons | 6/29/73 |
| 375,195 | Ion-Exchanged Transition Metal Catalysts for the Direct Oxidation of Olefins to Epoxy Alcohols | Lyons | 6/29/73 |
| 375,260 | Catechol from 1,2-Epoxy-3-Hydroxycyclohexane | Lyons | 6/29/73 |

These cases demonstrate the utility, as catechol and resorcinol intermediates, for certain of the products of this isomerization process.

BACKGROUND OF THE INVENTION

This invention relates to a novel process for the geometric isomerization of epoxy alcohols. More particularly, this invention is directed to the equilibration of geometrically isomeric cyclic epoxy alcohols using Group VIII metal complexes as catalysts.

SUMMARY OF THE INVENTION

It has been found, in accordance with the present invention, that geometrically isomeric cyclic epoxy alcohols may be equilibrated rapidly and selectively in the presence of a soluble metal complex of the formula $$L_x M^n X_y$$

wherein L is a neutral ligand such as CO; a mono-, di-, tri-, or tetradentate phosphine, e.g. $PPh_3$, where Ph is phenyl; a mono-, di-, tri-, or tetradentate arsine, e.g. $AsPh_3$; a mono-, di-, tri-, or tetradentate stibine, e.g. $SbPh_3$; a mono-, di-, tri-, or tetradentate amine, e.g. $NR_3$, where R is lower alkyl, cycloalkyl of 5-15 carbon atoms, aryl, or benzyl; an olefin, particularly alkenes and alkadienes such as ethylene, propylene, butadiene, cyclohexadiene, or cyclooctadiene; $x$ is an integer of from 0-6, but when $x$ is 2 or more, L may be the same or different; M is a metal of Group VIII of the Periodic Table, preferably Ru, Rh, Ir, and Os; $n$ is an integer of from 0-3 and denotes the valence state of the metal; X is an anionic ligand such as cyclopentadienyl, chloro, bromo, iodo, lower alkyl, benzoates, alkanoates, e.g. acetates, acetyl acetonates, cyano, thiocyanato, isothiocyanato, hydrido, hexafluorophosphate, tetrafluoroborate, trichlorostannato, pentachlorostannato, and the like; and $y$ is an integer of from 0-3, and is equal to $n$, but when $n$ is 0, then $x$ is equal to at least 1; but when either $x$ or $y$ is 0, then the other integer must be at least 1.

Use of the aforedescribed catalysts in the process of this invention is particularly advantageous in that the reaction proceeds rapidly in homogeneous solution using low concentrations of catalysts under mild conditions to selectively transform geometrical isomers of cyclic epoxy alcohols without destroying the sensitive oxirane ring.

DESCRIPTION OF THE INVENTION

The starting material may be any cyclic epoxy alcohol having at least two geometrically non-equivalent isomers which differ in the geometrical relationship between the hydroxyl group and the oxirane ring, and are interconverted by a change in only the geometry of either group. These epoxy alcohols have the structures (I) and (II) shown below and are isomerized by the process described by equation 1:

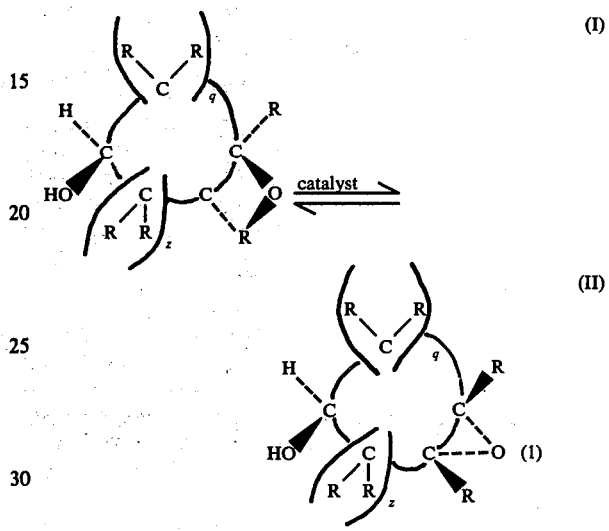

In the structures (I) and (II), the R groups are selected from the group consisting of hydrogen, lower alkyl, aralkyl, aryl, and the like, where the R groups in any given molecule may be the same or different; and q and z are integers denoting ring size and may vary from 0-7 but q plus z must equal at least 2. Included amongst these epoxy alcohols are such compounds as cis- and trans- 1,2-epoxy-3-hydroxycyclohexane, cis- and trans- 1,2-epoxy-4-hydroxycyclohexane, cis- and trans- 1,2-epoxy-3-hydroxycyclopentane, and cis- and trans- 1,2-epoxy-3-hydroxy-2-methylcyclohexane.

Examples of the isomerization reactions are illustrated below, (equations 2-5):

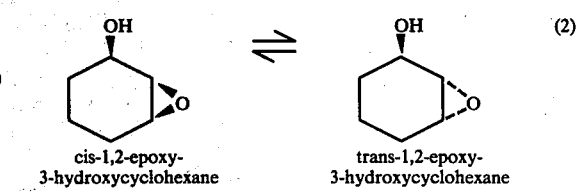

cis-1,2-epoxy-3-hydroxycyclohexane ⇌ trans-1,2-epoxy-3-hydroxycyclohexane (2)

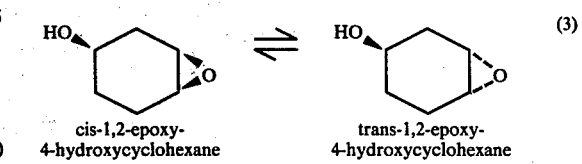

cis-1,2-epoxy-4-hydroxycyclohexane ⇌ trans-1,2-epoxy-4-hydroxycyclohexane (3)

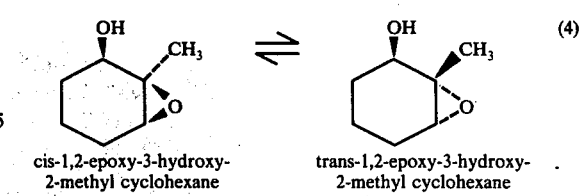

cis-1,2-epoxy-3-hydroxy-2-methyl cyclohexane ⇌ trans-1,2-epoxy-3-hydroxy-2-methyl cyclohexane (4)

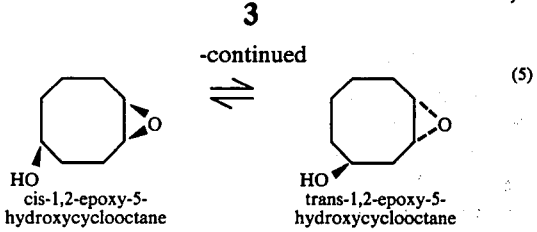

cis-1,2-epoxy-5-hydroxycyclooctane ⇌ trans-1,2-epoxy-5-hydroxycyclooctane (5)

The isomerization may conveniently be carried out by stirring a solution containing the epoxy alcohol and the catalyst at from 60°–160° C and preferably from 90-120° C for a period of from 15 minutes to 5 hours, although longer periods may be necessary to reach equilibrium in some cases, depending on the nature of the substrate and the catalyst. The molar ratio of catalyst to epoxy alcohol is from $10^{-4}$ - $10^{-1}$ and preferably is about $10^{-2}$, and the volume ratio of epoxy alcohol solvent is from 1 to 10, preferably 2 to 3. Typical solvents are any organic solvents which do not react with the epoxyol or the catalyst in an adverse way. These include benzene, toluene, tetrahydrofurane, chlorobenzene, O-dichlorobenzene, 1,2-dichloroethane, 1,1-dichloroethane and the like.

The preferred catalysts of this invention are soluble metal complexes of rhodium, ruthenium, osmium and iridium. Phosphine carbonyl complexes with hydrido ligands are very desirable in that they effect the desired transformation smoothly and rapidly at moderate temperatures with minimum production of unwanted by-products.

CATALYST PREPARATION

The Group VIII transition metal catalyst complexes employed herein are known compounds as shown in J. P. Collman, Accounts of Chemical Research, vol. I, pp. 136 to 143 (1968). These complexes may easily be prepared by simply reacting a suitable Group VIII metal halide with, e.g., a triaryl or trialkylphosphine or arsine in an alcoholic solvent such as methanol, and recovering the resulting complex therefrom.

The Group VIII transition metal catalyst complexes are also taught in P. S. Hallman, B. R. McGarvey and G. Wilkinson, J. Chem. Soc. (A), 1968, 3143 and J. C. Bailar and H. Italani, J. Am. Chem. Soc., 89, 1592 (1967) and related references. The tritriphenylphosphinechlororuthenium (II) hydride, for example, may be easily prepared by simply reacting the tristriphenylphosphineruthenium (II) dichloride with hydrogen in benzene-ethanol solution. The bistriphenylphosphine(-trichlorostannato)platinum (II) hydride may, if desired, be prepared in situ by reaction of hydrogen, stannous chloride and bistriphenylphosphineplatinum (II) dichloride in an alcoholic solvent such as methanol, the latter being a solvent solely for the catalyst components during in situ formation. The metal-phosphine complexes precursors to the hydride complexes are made by simply reacting a suitable Group VIII metal halide with a triaryl phosphine in an alcoholic solvent and recovering the resulting complex therefrom.

UTILITY

The oxidation of cyclohexene to epoxy alcohol or the epoxidation of 1-cyclohexene-2-ol either with per acids or with hydroperoxides and metal complexes gives mainly cis-1,2-epoxy-3-hydroxycyclohexane. Epoxy cyclohexanols are precursors of catechol and resorcinol. It is known that lithium aluminum hydride reduces the cis-epoxy alcohol preferentially to cyclohexane-1,2diol, catechol precursor (eq. 6); while the trans-isomer is preferentially reduced to cyclohexene-1,3-diol, a resorcinol precursor (eq. 7). Resorcinol and catechol are both articles of commerce and their selective formation is useful. Thus, ability to isomerize the cis- to the trans-epoxyalcohol in this case is useful in converting a potential catechol precursor into a potential resorcinol precursor.

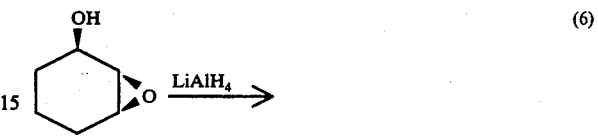
(6)

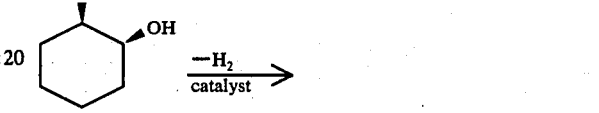

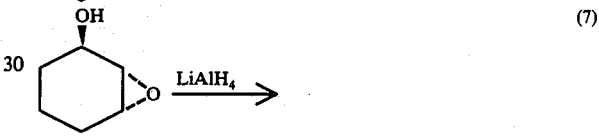
(7)

preferentially

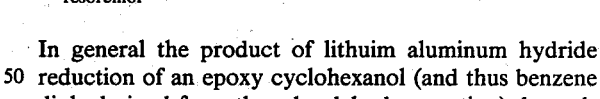

resorcinol

In general the product of lithuim aluminum hydride reduction of an epoxy cyclohexanol (and thus benzene diols derived from them by dehydrogenation) depends on the geometry of the starting epoxy cyclohexanol. Since in many cases conventional epoxidation procedures leading to epoxy alcohols give cis-products, a selective method of converting cyclic cis-epoxy alcohols to the trans-isomers has utility. Useful benzene diols obtained by such procedures include catechol, resorcinol, and others.

EXAMPLE 1 cis-1,2-epoxy-3-hydroxycyclohexane, 5.0 ml, in 10.0 ml toluene is stirred at 110° C for the time designated in the table below. The cis isomer is converted to the trans-1,2-epoxy-3-hydroxycyclohexane which is analyzed by glpc isolated by preparative glpc and whose structure is determined by a comparison of nmr, or and glpc retention time with an authentic sample:

TABLE

EQUILIBRATION OF cis- AND trans-1-HYDROXYCYCLOHEXENE OXIDE

| Catalyst(g.) | Reaction time, hr. | —OH | cis-V | trans-V | Other | cis-/trans- |
|---|---|---|---|---|---|---|
| Rh(H)(CO)(Ph₃P)₃(0.25) | 1 | — | 80.1 | 16.9 | 3.0 | 4.7 |
|  | 2 | — | 78.2 | 18.9 | 2.9 | 4.1 |
|  | 3 | — | 74.6 | 21.4 | 3.0 | 3.5 |
|  | 4 | — | 71.5 | 24.3 | 4.2 | 2.9 |
| Rh(H)(CO)(Ph₃P)₃(0.5) | 0.5 | 1.1 | 67.6 | 23.0 | 8.3 | 3.4 |
|  | 1.5 | 1.5 | 61.8 | 27.6 | 9.1 | 2.2 |
|  | 4 | 1.9 | 59.2 | 29.6 | 9.3 | 2.0 |
| Rh(H)(CO)(Ph₃P)₃(1.0) | 1 | 3.6 | 55.8 | 33.9 | 6.7 | 1.7 |
|  | 2 | 4.1 | 51.9 | 36.7 | 7.3 | 1.4 |
| Rh(H)(CO)(Ph₃P)₃(1.5) | 0.5 | 3.9 | 44.9 | 39.6 | 11.6 | 1.1 |
| RhCl₂(Ph₃P)₃(0.5) | 1 | 0.2 | 62.4 | 28.4 | 9.0 | 2.2 |
|  | 2 | 2.9 | 54.5 | 29.0 | 13.6 | 1.9 |
|  | 3 | 5.4 | 45.0 | 36.0 | 13.6 | 1.3 |
|  | 4 | 6.3 | 44.5 | 36.2 | 15.0 | 1.2 |
|  | 5 | 8.2 | 41.0 | 35.2 | 15.6 | 1.2 |
| RhCl(CO)(Ph₃)₄(1.0) | 3 | 1.0 | 76.0 | 16.3 | 6.7 | 4.7 |

EXAMPLE 2

In accordance with the procedures of Example 1, cis-1,2-epoxy-3-hydroxycyclohexane is isomerized to a mixture of cis- and trans-1,2-epoxy-3-hydroxycyclohexane using the iridium complexes: IrH₂Cl(Ph₃P)₂(CO), and IrH(CO)(Ph₃P)₃ at 100° C and IrCl(CO)(Ph₃P)₂ at 125° C.

EXAMPLE 3

In accordance with the procedures of Example 1 but substituting cis-1,2-epoxy-4-hydroxycyclohexane for cis-1,2-epoxy-3-hydroxycyclohexane rapid isomerization to the transisomer is achieved in the presence of each of RuCl₂(Ph₃P)₃ and RhH(CO)(Ph₃P)₃.

EXAMPLE 4

In accordance with the procedures of Example 1 but substituting o-dichlorobenzene for toluene as a solvent, cis-1,2-epoxy-3-hydroxycyclohexane is isomerized to the trans-isomer using each of the catalysts RhH(CO)(Ph₃P)₃, IrH(CO)(Ph₃P)₃, RuCl₂(Ph₃P)₃ and OsBr₂(Ph₃P)₄.

EXAMPLE 5

In accordance with the procedures of Example 1 but substituting cis-1,2-epoxy-3-hydroxycyclopentane for cis-1,2-epoxy-3-hydroxycyclohexane, the trans-1,2-epoxy-3-hydroxycyclopentane is obtained using RhH(CO) (Ph₃P)₃ as the catalyst.

EXAMPLE 6

In accordance with the procedures of Example 1 but substituting cis-1,2-epoxy-3-hydroxycycloheptane for cis-1,2-epoxy-3-hydroxycyclohexane the trans-1,2-epoxy-3-hydroxycycloheptane is obtained using RuCl₂(Ph₃P)₃ as the catalyst.

The invention claimed is:

1. A process for the geometrical isomerization of a cis-hexacyclic epoxy alcohol to the corresponding trans-form which comprises contacting said alcohol in the presence of a solvent with a catalyst of the formula $$L_x M^n X_y$$

wherein L is a neutral ligand; X is an anionic ligand; M is a group VIII metal selected from the group consisting of ruthenium, rhodium, osmium, and iridium; n is an integer of from 0–3 denoting the valence of the metal; x is an integer of from 0–6; and y is an integer of from 0–3 and is equal to n, but when n is 0, then x equals at least 1; but when either x or y is 0, then the other integer may be at least 1.

2. The process according to claim 1 wherein the neutral ligand L of the catalyst is CO; a mono-, di-, tri-, or tetradentate phosphine; a mono-, di-, tri-, or tetradentate arsine; a mono-, di-, tri-, or tetradentate stibine; a mono-, di-, tri-, or tetradentate amine; or an olefin; and the anionic ligand X is cyclopentadienyl; chloro; bromo; iodo; lower alkyl; a benzoate; an alkanoate; acetyl acetonate; cyano; thiocyanato; isothiocyanato; hydriodo; hexafluorophosphate; tetrafluoroborate; trichlorostannato; or pentachlorostannato.

3. The process according to claim 1 wherein the epoxy alcohol starting material is cis- 1,2-eopxy-3-hydroxycyclohexane, cis- 1,2-epoxy-4-hydroxycyclohexane, or cis- 1,2-epoxy-3-hydroxy-2-methycyclohexane.

4. The process according to claim 1 wherein the catalyst is Rh(H)(CO)(PPh₃)₃, RuCl₂(PPh₃)₃, RhCl(CO)(PPh₃)₂, IrH₂Cl(CO)(PPh₃)₂, IrH(CO)(PPh₃)₃, IrCl(CO)(PPh₃)₂, or OsBr₂(PPh₃)₄.

5. The process according to claim 1 wherein the reaction temperature is from 60°–160° C.

6. The process according to claim 1 wherein the mole ratio of catalyst to epoxy alcohol is from $10^{-4} - 10^{-1}$.

* * * * *